US006405450B1

(12) United States Patent
Wood et al.

(10) Patent No.: US 6,405,450 B1
(45) Date of Patent: Jun. 18, 2002

(54) GRADUATED SOLE-TAPE FOR FITTING IRON-TYPE GOLF CLUBS AND METHOD OF USING SAME

(75) Inventors: Donald C. Wood, Temecula; Todd D. Harman, Long Beach, both of CA (US)

(73) Assignee: Roger Cleveland Golf Company, Inc., Cypress, CA (US)

( * ) Notice: Subject to any disclaimer, the term of this patent is extended or adjusted under 35 U.S.C. 154(b) by 0 days.

(21) Appl. No.: 09/580,217

(22) Filed: May 26, 2000

Related U.S. Application Data

(60) Provisional application No. 60/141,312, filed on Jun. 25, 1999.

(51) Int. Cl.[7] .............................. G01B 3/10; A63B 69/36
(52) U.S. Cl. .............................. 33/759; 33/755; 33/758; 473/242
(58) Field of Search ........................... 33/755, 758, 759, 33/508; 473/226, 244, 245, 246, 242, 238

(56) References Cited

U.S. PATENT DOCUMENTS

| | | | | |
|---|---|---|---|---|
| 1,485,272 A | * | 2/1924 | Kinsman | 473/242 |
| 2,859,972 A | * | 11/1958 | Reach | 473/242 |
| 2,934,347 A | * | 4/1960 | Siniscalchi | 473/242 |
| 3,360,268 A | * | 12/1967 | Molinari | 473/244 |
| 3,621,579 A | * | 11/1971 | Dubitsky | 33/758 |
| 3,648,835 A | * | 3/1972 | Yucel | 33/755 |
| 3,845,955 A | * | 11/1974 | Solheim | 473/226 |
| 4,064,631 A | * | 12/1977 | Gebert | 33/755 |
| 4,425,391 A | * | 1/1984 | Wilson | 33/758 |
| 4,708,346 A | * | 11/1987 | Pierce et al. | 473/242 |
| 4,713,888 A | * | 12/1987 | Broselow | 33/759 |
| 4,977,680 A | * | 12/1990 | Marshall | 33/508 |
| 5,253,869 A | * | 10/1993 | Dingle et al. | 473/245 |
| 5,429,366 A | * | 7/1995 | McCabe | 473/242 |
| 5,433,446 A | * | 7/1995 | Lindstedt, Jr. | 473/242 |
| 5,452,523 A | * | 9/1995 | Jansen | 33/755 |
| 5,467,538 A | * | 11/1995 | Chou et al. | 33/508 |
| 5,480,151 A | * | 1/1996 | Adams | 473/238 |
| 5,582,552 A | * | 12/1996 | Hofmeister | 473/242 |
| 5,720,668 A | * | 2/1998 | Brett | 473/242 |
| 5,722,177 A | * | 3/1998 | Reilly, III | 33/508 |
| 5,950,321 A | * | 9/1999 | Pena et al. | 33/759 |
| 6,004,222 A | * | 12/1999 | Moody | 473/242 |
| 6,062,986 A | * | 5/2000 | Kaise | 473/242 |
| 6,082,018 A | * | 7/2000 | Wells | 33/759 |
| 6,217,077 B1 | * | 4/2001 | Priebe | 33/755 |
| 6,237,243 B1 | * | 5/2001 | Cook | 33/758 |

* cited by examiner

*Primary Examiner*—Diego Gutierrez
*Assistant Examiner*—Yaritza Guadalupe
(74) *Attorney, Agent, or Firm*—Parkhurst & Wendel, L.L.P.

(57) ABSTRACT

A sole-tape for use in fitting lie-angle of an iron-type golf club to an individual golfer, comprising a strip of thin, adhesive backed tape having dimensions generally corresponding to the area of the sole of an iron-type golf club head, the tape having sufficient integrity and the adhesive having sufficient adhesive strength to withstand and maintain the sole-tape on the sole of a club head throughout at least one impact with a surface upon which a golf ball may rest, the tape having thereon gradation or graduation lines each extending from a longitudinal edge of the tape, the gradation lines curving concavely away from the end of said sole-tape corresponding to the toe of the golf club, with spacing between adjacent gradation lines corresponding to a correlated amount of lie-angle correction, and a location marking for alignment of the sole tape with a certain feature on a golf club head.

23 Claims, 3 Drawing Sheets

GRADUATED SOLE-TAPE FOR FITTING IRON-TYPE GOLF CLUBS AND METHOD OF USING SAME

CROSS-REFERENCE TO RELATED APPLICATIONS

This application claims the benefit of the Jun. 25, 1999 filing date of U.S. Provisional Patent Application Serial No. 60/141,312.

FIELD OF THE INVENTION

This invention relates to custom-fitting iron-type golf clubs to a particular golf player, and to a unique sole-tape for use in club fitting, and method for using that unique sole-tape.

BACKGROUND OF THE INVENTION

Since different individual golfers will have different height, leg length, arm length, body configuration, swings, and swing actions, it is well known that to function properly, golf clubs should be "fitted" to the individual player. Proper fitting will result in a "prescription" which will uniquely characterize a particular set of golf clubs so that they will function properly when hit by the golfer whom that prescription fits. Among the variables which may be specified in such a golf club prescription are total club length, shaft type and flex, grip size, golf club head design and lie angle.

The present invention is particularly focused on an improvement in fitting the lie angle of iron-type golf clubs. A face view of the club head 10 of an iron-type golf club is illustrated in FIG. 1, which also shows the "lie angle" of that club head, which is the angle 11 defined between the horizontal ground plane H and the axis 12 of the hosel 13 and/or shaft 14 of the club, when that axis lies in a vertical plane which is perpendicular to another vertical plane, which is perpendicular to the club face and corresponding to straight lines of flight from the club face in the direction of a desired shot hit from that club face, i.e., a so-called target line plane. In the illustration of FIG. 1, that target line plane would be perpendicular to the paper on which FIG. 1 is drawn and emerging out of the paper toward the reader from the center of the illustrated club face. It will be appreciated that by tilting the club shaft and hosel somewhat upwardly or downwardly as indicated by arrows 15, the lie-angle will increase or decrease, respectively, and the "lie" of the sole 16 of the club will be varied vis-a-vis horizontal plane H, which corresponds to horizontal turf upon which would lie a ball to be hit by the club head.

If a golf club is properly fit for a given player, when the club is swung by that player using his typical swing, at or about the point of ball impact the sole of the club will also impact the turf. The sole of most golf clubs is at least slightly curved from toe 17 to heel 18 of the club head, defining so-called "sole radius," and also is curved or rounded in the fore to aft direction, that is from the leading edge 19 of the sole to the trailing edge 20 of the sole as illustrated in bottom view FIG. 2, this curvature corresponding to a so-called "bounce radius" or "sole camber." A properly fitted iron-type golf club should impact the turf at about the middle of the length of the sole if the lie angle is properly fitted.

In the past, fitting of the lie angle of an iron-type golf club has been facilitated by using either a plain sole tape or a tape partitioned into small squares, with one side of the small squares lying substantially parallel to the leading edge of the sole of an iron upon which the sole-tape is being used. The sole-tape is used by temporarily, usually for no more than one shot, applying the tape, which comprises an adhesive-backed thin film applied temporarily to cover substantially the entire area of the sole of an iron-type golf club being fitted to a particular golfer. Once applied, the golfer then hits a ball from a relatively hard surface which leaves a test scar on the tape evidencing that portion of the sole of the club which impacted the hard surface at or about the time the club head also hit the ball. The resultant test scar may be located anywhere along the heel to toe length of the sole-tape. As suggested above, the preferred location of the scar is in the middle of the sole, although it is common for the scar to be located off-center toward the heel or toe of the club thus indicating an ill-fitted club for the golfer who used it in creating the scar.

The forms of prior sole-tapes included those partitioned into small squares as an attempt to correlate test scar location with re-fitting the particular golf club head to the body and swing of a particular golfer. In use, the resultant test scar on such a sole-tape is supposed to be located in a square section of the tape that corresponds to a particular lie angle re-fitting specification.

However, even with prior art sole-tapes partitioned into small squares, which squares are correlated to proposed changes in lie angle, there remain other inherent uncertainties in the use of such sole-tapes for fitting of lie angle of iron-type golf clubs. For example, as the face angle, i.e., heel to toe direction, of the club face changes from any orientation other than square, that is perpendicular to the target line plane, the relationship between the lie of the sole of the club vis-a-vis the underlying turf or surface will be affected. If a test shot using a lie tape is hit with an open (slice) face, the position of the test scar on the lie tape will be distorted and mislocated vis-a-vis a preferred central scar location. Similarly, the test scar created by a shot executed with a more closed (hook) club face will likewise be a scar whose position on the lie tape will be erroneously located vis-a-vis a desired centrally located scar. The erroneous location of test scars on lie-angle fitting sole-tapes, and erroneous correlations between square markings on such prior tapes result in the production or re-fitting of the lie angles of iron-type golf clubs which is still substantially incorrect and ineffective.

BRIEF SUMMARY OF THE INVENTION

The present invention is designed to overcome such shortcomings and defects in prior art lie-fitting sole-tape systems. In the present invention, the sole-tape is specially marked with gradation or graduation markings which are not merely lines perpendicular to the leading edge of the sole of the club, or squares including such lines, but are curved lines wherein the ends of each such gradation line where each such gradation line intersects the leading edge and trailing edge, respectively, of the sole of the club are closer to the toe and farther from the heel of the club than the center portions of those lines. This special form of curved gradation or graduation line adapts the gradation line so that it still properly correlates to a desired degree of correction of lie angle even when a test scar located on or adjacent that gradation line on a sole-tape after club testing may indicate that the particular test scar was created by a swing in which the face of the club was too closed or too open at the time of ball impact and test scarring, or the entire club head was tilted too far backward or tilted too far forward, that is too upright, at the time of the test swing and creation of the test scar. When the advantageous graduated sole-tape of the present invention is used, it is typically unnecessary to make further corrections in correlation between the lie-angle corrections suggested directly by the marking on the sole-tape corresponding to the specially shaped curved gradation lines, as often was the case with prior art sole-tapes.

BRIEF DESCRIPTION OF THE DRAWINGS

The foregoing advantages and further features of the present invention will be understood from the following drawings, which include illustrations of preferred embodiments of the advantageous system of the present invention, wherein.

DETAILED DESCRIPTION

Figure 3:
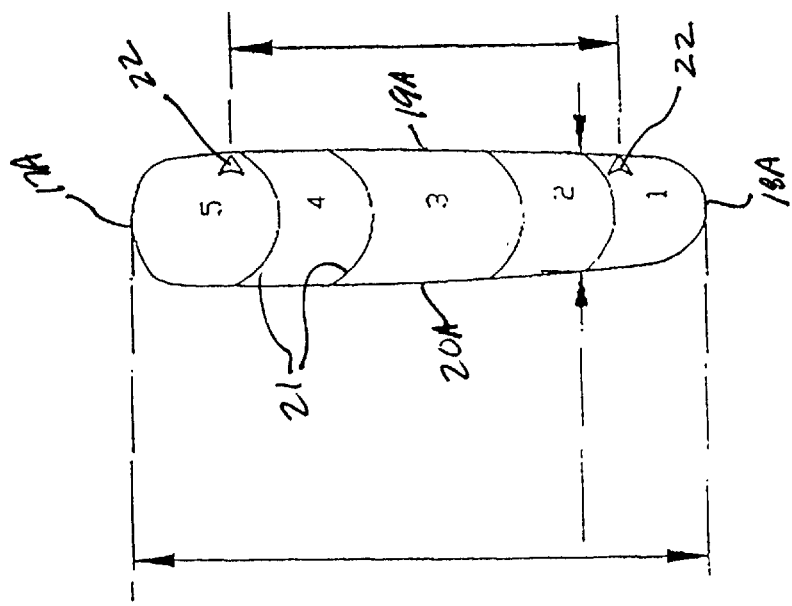
FIG. 3 is a plan view of an advantageous sole-tape of the present invention.
Figure 6D:
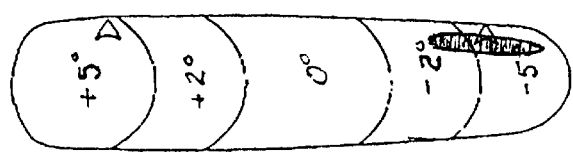
FIG. 6D is a plan view of another inventive sole-tape bearing a test scar indicating that at the time of impact the face of the test club head was too closed and not flat enough, i.e., tilted somewhat heelward, resulting in scarring at the leading edge of the heel of the club.
Figure 6C:
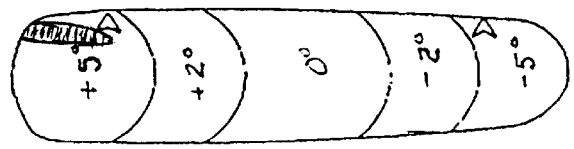
FIG. 6C is a plan view of another inventive sole-tape bearing a test scar indicating that at the time of impact the face of the test club head was too closed and the test club head was too flat, i.e., tilted somewhat toe-ward.
Figure 6B:
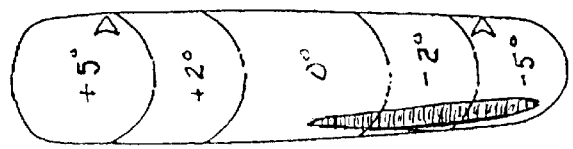
FIG. 6B is a plan view of another inventive sole-tape bearing a test scar indicating that at the time of impact the face of the test club head was too open.
Figure 6A:
FIG. 6A is a plan view of another inventive sole-tape bearing a test scar indicating that at the time of impact the face of the test club head was too closed.
Figure 5:
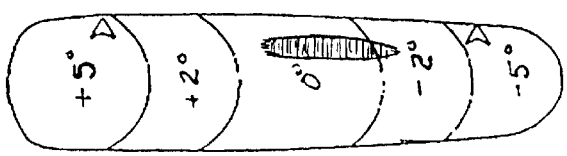
FIG. 5 is a plan view of a sole tape of the present invention showing a test scar in a location thereon indicating that the lie angle of the club which created the test scar is proper for the player who used the club in the test which created the test scar.

The advantageous sole-tape of the present invention is illustrated, in plan view, in FIG. 3. The sole-tape comprises a thin film of material, typically a thin film of plastic material, that may be either transparent or opaque, and which bears an adhesive layer on its reverse side, which adhesive is sufficient to at least temporarily adhere the sole-tape to the sole of an iron-type golf club and maintain the tape thereon during at least one test swing in which the sole of the club bearing the sole-tape, and thus the sole-tape itself, impact a substantially horizontal surface thereby abrading a portion of the sole-tape creating a test scar thereon as a result of such abrasive impact. In one embodiment the inventive lie-tape comprises a thin, adhesive-backed film having a metallic coating thereon with the exterior surface of the metallic coating overlaid by a darker coating wherein the gradation or graduation lines are metallic uncoated areas, i.e., the lines and indicia shown in FIGS. 3, 5 and 6, for example are negative images formed by the metallic coating exposed in areas of the inventive lie-tape not bearing the darker outer coating.

The upper surface of the sole-tape illustrated in FIG. 3 is marked with specially shaped gradation or graduation lines 21, the number of which lines may vary, particularly with respect to the specific increments of lie angle correction which the user desires to have indicated directly on the sole-tape, as distinct from some data which correlates the location of test scars on a sole-tape with one or more gradation lines on the tape. In that regard, the individual gradation or graduation lines, or the regions between the lines, may be numbered, for example, numbered consecutively as indicated in FIG. 3, or may be numbered with a net line angle (NLA) outwardly from the central sector, the location of desired test scars. For example, the central sector could remain unnumbered or bear numeral 0, and then lines or sectors moving toward the toe location on the sole-tape could be designated +2°, +4°, +6°, for example, indicating the need to correct lie angle by increasing lie angle by a corresponding amount. Similarly, the special calibration lines or sectors between lines in the heel direction from the central sector of the sole-tape could be numbered −2°, −4°, −6°, for example, indicating that test scars located in such regions call for the need to correct lie angle by decreasing the lie angle of the club upon which the test was used and resulted in test scars in such regions of the sole-tape. A similar progression is illustrated in FIGS. 4, 5 and 6A–D.

Figure 1:
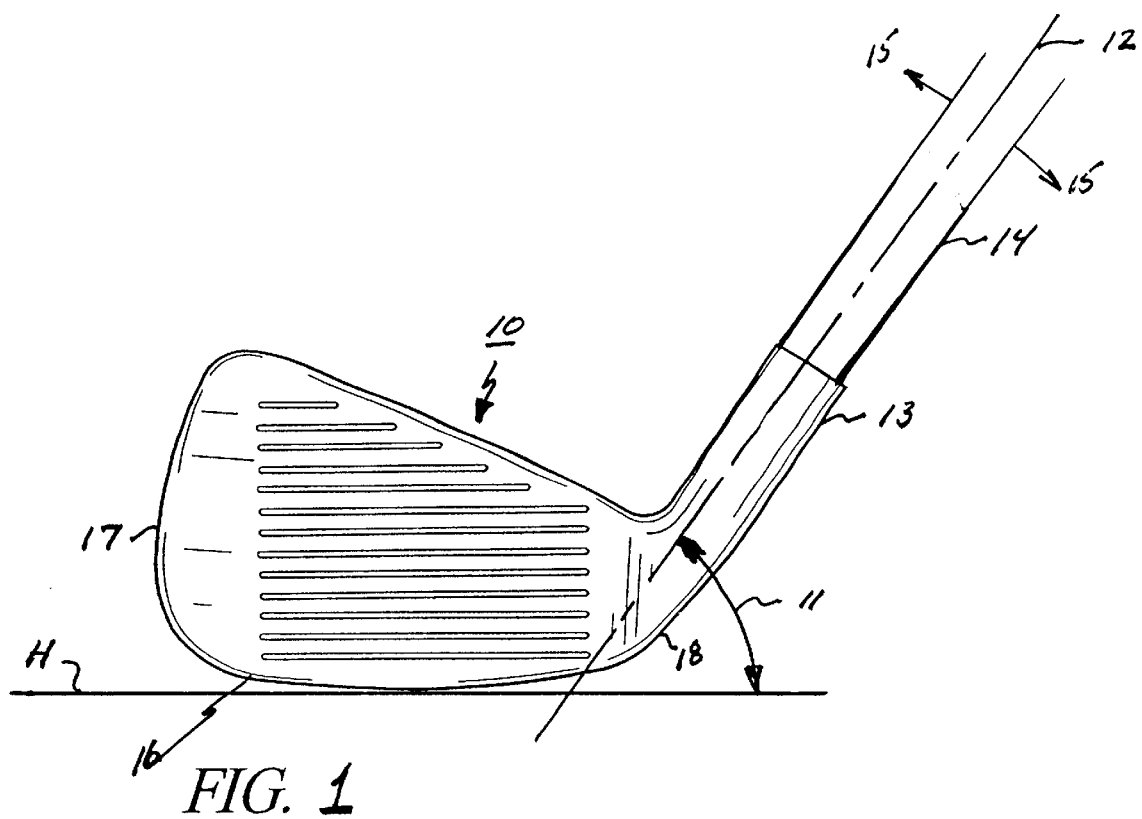
FIG. 1 is a face view of a club head and portion of a shaft of an iron-type golf club.
Figure 2:
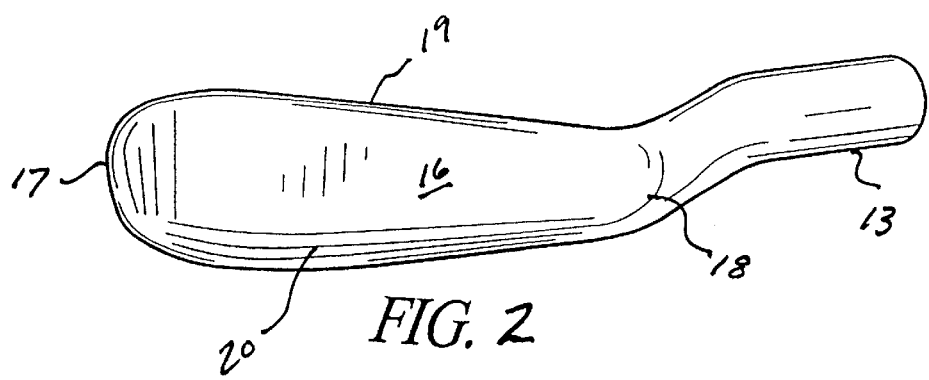
FIG. 2 is a bottom or sole view of an iron-type golf club head such as that illustrated in FIG. 1.

The sole-tape of FIG. 3 has been marked with reference numerals 17A and 18A corresponding to the toe 17 and heel 18, respectively, of an iron-type golf club such as that illustrated in FIGS. 1 and 2, and 19A and 20A corresponding to the leading edge and trailing edge respectively, of the sole 16 of an iron-type golf club such as that illustrated in FIGS. 1 and 2.

Figure 4:
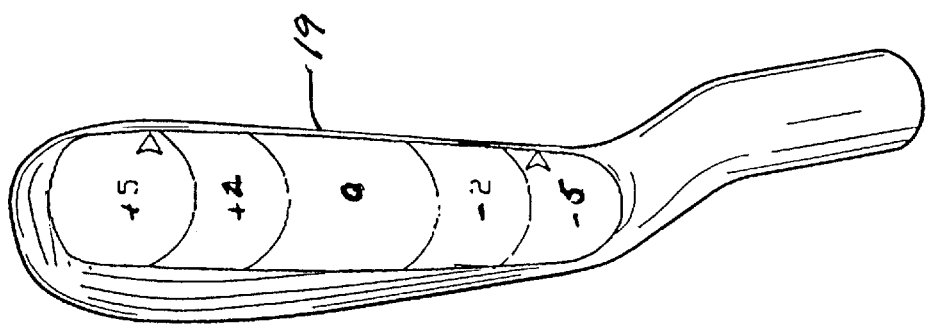
FIG. 4 is a bottom or sole view of an iron-type golf club head, like the view of FIG. 2, but whereupon the advantageous sole-tape of the present invention, as illustrated in FIG. 3, has been installed for use on the sole of the club head.

When applied to the sole of an iron-type golf club to be tested, as illustrated in FIG. 4, the advantageous lie-tape of the present invention typically has at least a portion of its leading edge 19A applied overlapping or very closely parallel to a corresponding portion of the leading 19 edge of the sole of the club head. And, the inventive lie-tape may include one or more markings, here illustrated as arrow heads or chevrons 22, which can be aligned with a designated portion of the club head, such as the end point(s) of one or more score lines on the face of the club head. More specifically, the location of marking 22 may lie in a plane substantially perpendicular to the leading longitudinal edge of the sole tape for application of the sole-tape to the sole of an iron-type golf club head so that a corresponding point in a score line on the hitting face portion of the club head, such as the end of a score line, also lies in that plane.

In the advantageous sole-tape of the present invention, the uniquely curved shape of the gradation or graduation lines 21 makes the inventive sole-tape particularly efficiently useful for the golf professional or other person assisting a golfer in determining the optimum lie angle to which that golfer's clubs should be manufactured or adjusted. In prior art sole-tapes using gradation lines, the lines were straight and perpendicular to the leading edge 19A of the tape and the club head upon which the tape was used, but those straight lines did not appropriately account for the adverse effects of deviations of club face angle from normal or perpendicular to a plane also containing the desired target, and the corresponding errors created in attempting to correlate resultant test scars on such straight line sole-tapes with proper corrections in lie angle to provide the particular golfer clubs manufactured or adjusted to lie angles most appropriate for that golfer's swing.

However, the unique gradation or graduation lines on the advantageous sole-tapes of the present invention,. wherein both the leading edge ends and trailing edge ends of the lines are curved outwardly in the toe-ward direction of the sole of a club upon which the inventive sole-tapes are to be used, automatically compensate for swings wherein the club face is too open or too closed, or the club head too upright or too flat at the moment of ball impact and test scarring of the sole tape during club fitting. This improvement results in more reliable data for more reliably prescribing the proper lie angle for the golfer whose test swings created the test scars on the advantageous sole-tapes of the present invention, thus enabling the club vendor or club fitter to provide the golfer/customer with a set of iron-type golf clubs more custom tailored to that golfer/customer's swing, thereby hopefully making such custom fitted clubs more consistently functional for that golfer/customer.

It will be appreciated that each set of correlated iron-type golf club heads will preferably have a corresponding sole-tape with gradation lines thereon which are uniquely located for properly calibrating lie angle of the iron-type golf club heads of that particular correlated set. Indeed, it would be possible to have a single unique sole-tape for fitting the lie angle of each individual club, although a correlated set of clubs is typically so similar in design and inertial behavior that a single sole-tape configuration will typically perform satisfactorily in facilitating lie angle correction of all clubs in that correlated set.

In use, the advantageous sole-tape of the present invention is applied to the sole of an iron-type golf club head to which the gradation or graduation lines on the tape are particularly correlated, with the leading edge line 19A of the tape lying along the leading edge 19 of the sole of the club (see FIGS. 2 and 4), with the tape otherwise being centered on the sole with the tip of the heel 18A of the tape lying at the tip of the heel 18 of the club head, the tip of the toe of the tape 17A lying at the toe end 17 of the sole of the club, and the trailing edge 20A of the tape lying at the trailing edge 20 of the sole of the club. The golfer who seeks to have the lie angle of such club heads custom fitted for his swing then hits a golf ball located on a firm, horizontal surface, using the golf club to which the sole-tape is applied as described above. A single swing of that golfer, impacting a golf ball on a firm horizontal surface, will also result in impact of the sole of the iron-type golf club head with the firm horizontal surface at about the time the ball is impacted by the club head, and that impact with the horizontal surface will abrasively scar the sole-tape at some location along its length, and the location of that scar vis-a-vis the correlated gradation or graduation lines on the tape immediately provides data to the club fitter for adjustment of the lie angle of the club head upon which the test was conducted. With the advantageous system of the present invention it is unnecessary to consult any other set of data corresponding to particular gradation lines or squares on the sole-tape, because the lines on the particular sole tape are already correlated and calibrated to corresponding net lie angle adjustments as indicated by the numbers on the sole-tape itself.

Sometimes a test scar will lie in a single region between gradation lines on the inventive lie-tape. However, often a test scar will lie across a gradation or graduation line and in two adjacent different regions so that the club fitter using the inventive lie-tape will need to choose between the two net lie angle correction values indicated in the two adjacent regions in which the test scar lies. Usually, the scar will be more predominant in one region which will indicate the desired net lie angle correction. But sometimes the club fitter may find it desirable to re-test by having the player hit different clubs corresponding to each of the two adjacent net lie angle corrections to determine which is actually preferable for that player's swing.

Those skilled in the art of club fitting will appreciate that minor changes in the exact shape of the lie-tape, the number of gradation or graduation lines thereon, and the like can be made within the scope of the present invention without departing from the scope and spirit of the invention, which is defined by the following claims.

What is claimed is:

1. A sole-tape for use in fitting lie-angle of an iron-type golf club to an individual golfer, said sole-tape comprising:

a strip of thin tape base material having a layer of adhesive material on one major surface thereof, said strip being substantially planar and having dimensions corresponding in size and shape to the area of the sole of an iron-type golf club head to be tested for lie-angle fitting using said sole-tape;

the tape base material having sufficient integrity and the adhesive having sufficient adhesive strength to withstand and maintain the sole-tape on the sole of an iron-type golf club head throughout at least one impact with a generally horizontal surface upon which a golf ball may rest, and one major surface of said strip of tape base material having thereon gradation indicia corresponding to a graduated amount of lie-angle correction to be made in a corresponding iron-type golf club head, wherein the graduation indicia are arranged to cooperate with a club head face-angle.

2. The sole-tape of claim 1 wherein said gradation indicia are gradation lines each generally extending from a longitudinal edge of said strip which corresponds to a leading edge of an iron-type golf club and extending toward the opposite longitudinal edge of said strip which corresponds to the trailing edge of the sole of an iron-type golf club, with spacing between adjacent gradation lines corresponding to a correlated amount of lie-angle correction to be made in a corresponding iron-type golf club head.

3. The sole-tape of claim 2 additionally comprising correction indicia in at least one of said spacings indicating a specific amount of lie-angle correction.

4. The sole-tape of claim 3 wherein said correction indicia are present in a plurality of said spacings and each of said indicia corresponds to a specific amount of lie-angle increase or decrease to be made.

5. The combination of an iron-type golf club head comprising a clubhead body having face, back, toe, heel, sole and hosel portions, and having on the sole thereof a sole-tape according to claim 4.

6. The combination of an iron-type golf club head comprising a clubhead body having face, back, toe, heel, sole and hosel portions, and having on the sole thereof a sole-tape according to claim 3.

7. The combination of an iron-type golf club head comprising a clubhead body having face, back, toe, heel, sole and hosel portions, and having on the sole thereof a sole-tape according to claim 2.

8. The combination of an iron-type golf club head comprising a clubhead body having face, back, toe, heel, sole and hosel portions, and having on the sole thereof a sole-tape according to claim 1.

9. The combination of an iron-type golf club head comprising a clubhead body having face, back, toe, heel, sole and hosel portions, and having on the sole thereof a sole-tape according to claim 8.

10. A sole-tape for use in fitting lie-angle of an iron-type golf club to an individual golfer, said sole-tape comprising:

a strip of thin tape base material having a layer of adhesive material on one major surface thereof, said strip being substantially planar and having a leading longitudinal edge corresponding in length to at least a part of a leading edge of the sole of an iron-type golf club head to be tested for lie-angle fitting using said sole-tape, the tape base material having sufficient integrity and the adhesive having sufficient adhesive strength to withstand and maintain the sole-tape on the sole of an iron-type golf club head throughout at least one impact with a generally horizontal surface upon which a golf ball may rest, and one major surface of said strip of tape base material having thereon gradation lines each extending from the longitudinal edge of said strip which corresponds to a leading edge of an iron-type golf club and extending substantially toward an opposite trailing longitudinal edge of said strip, said gradation lines curving concavely away from the end of said sole-tape corresponding to the toe of an iron-type golf club, with spacing between adjacent gradation lines corresponding to a correlated amount of lie-angle correction to be made in a corresponding iron-type golf club head.

11. The sole tape of claim 10, additionally comprising a location marking for alignment of the sole-tape with a certain feature of an iron-type club head upon which the sole-tape is to be used.

12. The sole-tape of claim 11 additionally comprising correction indicia in at least one of said spacings indicating a specific amount of lie-angle correction.

13. The sole-tape of claim 12 wherein said correction indicia are present in a plurality of said spacings and each of said indicia corresponds to a specific amount of lie-angle increase or decrease to be made.

14. The combination of an iron-type golf club head comprising a clubhead body having face, back, toe, heel, sole and hosel portions, and having on the sole thereof a sole-tape according to claim 13.

15. The combination of an iron-type golf club head comprising a clubhead body having face, back, toe, heel, sole and hosel portions, and having on the sole thereof a sole-tape according to claim 12.

16. The sole-tape of claim 11, wherein the location marking lies in a plane substantially perpendicular to the leading longitudinal edge of the sole tape for application of the sole-tape to the sole of an iron-type golf club head so that a corresponding point in a score line on the hitting face portion of such a club head also lies in said plane.

17. The combination of an iron-type golf club head comprising a clubhead body having face, back, toe, heel, sole and hosel portions, and having on the sole thereof a sole-tape according to claim 16.

18. The combination of an iron-type golf club head comprising a clubhead body having face, back, toe, heel, sole and hosel portions, and having on the sole thereof a sole-tape according to claim 11.

19. The sole-tape of claim 10, wherein the substantially planar strip has dimensions corresponding in size and shape to the area of the sole of an iron-type golf club to be tested for lie-angle fitting using said sole-tape.

20. The combination of an iron-type golf club head comprising a clubhead body having face, back, toe, heel, sole and hosel portions, and having on the sole thereof a sole-tape according to claim 14.

21. The combination of an iron-type golf club head comprising a clubhead body having face, back, toe, heel, sole and hosel portions, and having on the sole thereof a sole-tape according to claim 10.

22. A sole-tape for use in fitting lie-angle of an iron-type golf club to an individual golfer, said sole tape comprising:

a strip of thin tape base material having a layer of adhesive material on one major surface thereof, said strip being substantially planar and having dimensions corresponding in size and shape to the area of the sole of an iron-type golf club head to be tested for lie-angle fitting using said sole-tape, the tape base material having sufficient integrity and the adhesive having sufficient adhesive strength to withstand and maintain the sole-tape on the sole of an iron-type golf club head throughout at least one impact with a generally horizontal surface upon which a golf ball may rest, and one major surface of said strip of tape base material having thereon gradation lines each extending from a longitudinal edge of said strip which corresponds to a leading edge of an iron-type golf club and extending substantially to the opposite longitudinal edge of said strip which corresponds to the trailing edge of the sole of an iron-type golf club, said gradation lines curving concavely away from the end of said sole-tape corresponding to the toe of an iron-type golf club, with spacing between adjacent gradation lines corresponding to a correlated amount of lie-angle. correction to be made in a corresponding iron-type golf club head, and correction indicia in at least one of said spacings indicating a specific amount of lie-angle correction, and a location marking for alignment of the sole tape with a certain feature on an iron-type golf club head upon which the sole-tape is to be used.

23. The combination of an iron-type golf club head comprising a clubhead body having face, back, toe, heel, sole and hosel portions, and having on the sole thereof a sole-tape according to claim 22.

* * * * *